United States Patent [19]

Yamada et al.

[11] Patent Number: 4,880,739
[45] Date of Patent: Nov. 14, 1989

[54] METHOD OF CULTIVATION OF PSEUDOMONAS BACTERIA

[75] Inventors: Hideaki Yamada, 19-1, Matsugasaki-Kinomoto-Cho, Sakyo-Ku, Kyoto-Shi; Kanehiko Enomoto, Yokohama; Ichiro Watanabe, Yokosuka, all of Japan

[73] Assignees: Hideaki Yamada, Kyoto; Nitto Kagaku Kogyo Kabushiki Kaisha, Tokyo, both of Japan

[21] Appl. No.: 104,566

[22] Filed: Oct. 2, 1987

Related U.S. Application Data

[63] Continuation of Ser. No. 551,949, Nov. 15, 1983, abandoned.

[30] Foreign Application Priority Data

Nov. 16, 1982 [JP] Japan ................................ 57-199750

[51] Int. Cl.⁴ ........................ C12P 13/02; C12N 1/20; C12K 1/38
[52] U.S. Cl. ................................. 435/129; 435/253.3; 435/874

[58] Field of Search ............... 435/129, 250, 253, 874, 435/253.3

[56] References Cited

PUBLICATIONS

Agric. Biol. Chem., 46 (5), 1183–1189, 1982 "A new Enzymatic Method of Acrylamiele Production", Yasuhisa Asano et al.
J. Gen. Microbiol. (1962), 27, 805–816, "An Inducible Amidose" Produced by a Strain of *Pseudomonos Aueruginosa*.

Primary Examiner—J. E. Tarcza
Attorney, Agent, or Firm—Emmanuel J. Lobato; Robert E. Burns

[57] ABSTRACT

Cells of Pseudomonas bacteria having a high nitrile hydratase activity can be obtained in a high yield by adding sequentially to a culture medium at least one compound selected from the group consisting of propionitrile, isobutyronitrile, propionamide, and isobutyramide in the process of cultivation of Pseudomonas bacteria capable of producing nitrile hydratase.

11 Claims, No Drawings

METHOD OF CULTIVATION OF PSEUDOMONAS BACTERIA

This is a continuation of copending application Ser. No. 551,949, filed Nov. 15, 1983.

BACKGROUND OF THE INVENTION

The present invention relates to a method of producing in a high yield cells of Pseudomonas bacteria having a high nitrile hydratase activity.

In recent years, there have been increasing attempts to utilize microorganisms and enzymes as they are or in an immobilized state as catalysts for various single or complex chemical reactions.

Nitrile hydratase has been found by Hideaki Yamada, one of the present inventors, et al. as an enzyme capable of hydrating nitriles to produce the corresponding amides. (Reference: Agric. Biol. Chem. 46 1165 (1982)) As one example of the utilization of this enzyme, a method for preparation of acrylamide from acrylonitrile in the presence of bacteria having nitrile hydratase has been proposed. (References: Japanese Patent Laid-Open Pub. No. 86093/1983 (Japanese Patent Appln. No. 184688/1981) and Agric. Biol. Chem. 46 1183 (1982))

Under these circumstances, a method that can ensure the production of cells of Pseudomonas bacteria having a high nitrile hydratase activity in a high yield would be remarkably beneficial.

SUMMARY OF THE INVENTION

An object of the present invention is to solve the above problem by adding to a culture medium a specific substance, i.e., at least one enzyme inducing agent selected from propionitrile, isobutyronitrile, propionamide, and isobutyramide in a specific manner, i.e., "sequentially" (as defined hereinafter), in the process of cultivation of the bacteria.

Thus, a distinguishing feature of the method for cultivation of Pseudomonas bacteria having a high nitrile hydratase activity according to this invention is the sequential addition of at least one compound selected from the group consisting of propionitrile, isobutyronitrile, propionamide, and isobutyramide to a culture medium in the preparation of cells of bacteria having nitrile hydratase activity by cultivating Pseudomonas bacteria capable of producing nitrile hydratase.

We have found that, by adding one or more of the enzyme inducing agents designated above to the culture medium sequentially during the cultivation of bacteria of the genus Pseudomonas, the nitrile hydratase activity per unit culture fluid increases remarkably. For example, the sequential addition of the enzyme inducing agent can increase the nitrile hydratase activity per unit culture fluid to a value nearly twice that obtained when the same compound is added at one time.

This increase in nitrile hydratase activity per unit culture fluid is presumably traceable to the increase in cell concentration (i.e., yield) and cell activity (i.e., quantity of the nitrile hydratase in the cells).

In the present invention, the propionitrile and other compounds named hereinbefore are sometimes called enzyme inducing agents in view especially of the latter factor although these compounds are effective not only in increasing the cell activity as has been set forth above.

DETAILED DESCRIPTION OF THE INVENTION

Pseudomonas Bacteria

The bacteria used in the present invention are Pseudomonas bacteria having nitrile hydratase activity and the capability of hydrating nitriles, particularly acrylonitrile, to produce the corresponding amides, particularly acrylamide. Specific examples of such bacteria are *Pseudomonas chlororaphis*, strain B 23 (FERM BP-187), and Pseudomonas sp., strain PS 1 (FERM BP-188), disclosed in Japanese Patent Laid-Open Pub. No. 86093/1983. The principal mycological properties of these bacteria are as follows.

| | | B 23 | PS 1 |
|---|---|---|---|
| | | (a) Morphology | |
| 1 | Shape and size of cell | bacillus 0.8–1.1 × 1.6–2.7 μm | bacillus 0.8–1.1 × 1.3–1.9 μm |
| 2 | Polymorphism | none | none |
| 3 | Motility | motile one to three polar flagella | motile with polar flagella |
| 4 | Formation of spores | none | none |
| 5 | Gram staining | − | − |
| 6 | Acid-fast property | − | − |
| | | (b) Growth on various culture media | |
| 1 | Bouillon-agar plate culture | spherical, convex, glossy, translucent and yellow | smooth, homogeneous, glossy, and mucoidal |
| 2 | Bouillon-agar slant culture | small colony formed | smooth, glossy, translucent, and yellow |
| 3 | Bouillon liquid culture | precipitated | |
| 4 | Bouillon-gelatin stab culture | liquified (+) | − |
| 5 | Litmus-milk | acidic: peptonized, not coagulated | alkaline: peptonized, not coagulated |
| | | (c) Physiological properties | |
| 1 | Reduction of nitrate | + | − |
| 2 | Denitrification | + | − |
| 3 | MR test | − | − |
| 4 | VP test | − | − |
| 5 | Formation of indole | − | − |
| 6 | Formation of hydrogen sulfide | − | − |
| 7 | Hydrolysis of starch | − | − |
| 8 | Utilization of citric acid | Simon's culture: + | Simon's culture: + |
| 9 | Utilization of inorganic nitrogen source | ammonium salt: + | ammonium salt: + |
| 10 | Formation of pigments | King-A culture: − King-B culture: + green (water-soluble) | King-A culture: − King-B culture: + green (water-soluble) |
| 11 | Urease | − | − |
| 12 | Oxidase | + | + |
| 13 | Catalase | + | + |
| 14 | Growth range | pH: 6.0–9.9 | |

| | B 23 | | PS 1 | |
|---|---|---|---|---|
| | temperature: 5–36.5° C. | | | |
| 15 Behavior toward oxygen | aerobic | | aerobic | |
| 16 O-F Test | oxidized | | oxidized | |
| 17 Formation of acid & gas from saccharide | Formation of acid | Formation of gas | Formation of acid | Formation of gas |
| D-glucose | + | − | + | − |
| D-mannose | + | − | + | − |
| D-fructose | − | − | − | − |
| D-galactose | + | − | + | − |
| maltose | − | − | − | − |
| sucrose | − | − | − | − |
| lactose | − | − | − | − |
| trehalose | | | − | − |
| D-mannitol | − | − | − | − |
| glycerol | − | − | − | − |
| starch | − | − | − | − |
| 18 Nutritive requirements | none | | none | |
| 19 Other properties | See remarks | | | |

Remarks:

| | |
|---|---|
| Aminopeptidase | + |
| Formation of levan from saccharose | + |
| Formation of poly-β-hydroxybutyrate | − |
| GC content | 64.6% |

Enzyme Inducing Agent

In the present invention, propionitrile, isobutyronitrile, propionamide, and isobutyramide are used as enzyme inducing agents. These compounds can be used singly or in the form of a mixture of two or more members.

In accordance with the present invention, these compounds are added to the culture medium sequentially. The term "sequentially" as used herein is intended to mean both "continuously" and "intermittently" and not "at one time in a single batch".

Cultivation—Practice of the Present Invention

A preferred embodiment of this invention will be described below.

Pseudomonas bacteria having nitrile hydratase activity are inoculated into a culture medium, especially an aqueous culture medium, containing carbon sources such as glucose, fructose, sucrose, dextrins, glycerol, ethanol, and succinic acid; nitrogen sources such as ammonia, ammonium sulfate, ammonium chloride, ammonium nitrate, and urea; organic nutriment sources such as yeast extract, meat extract, malt extract, casein hydrolyzate, and peptone; inorganic salts such as phosphates; magnesium, potassium, and iron and other metals in trace amounts; and other substances. Cultivation is carried out under aerobic conditions while at least one of propionitrile, isobutyronitrile, propionamide, and isobutyramide is added sequentially as an enzyme inducing agent.

The sequential addition of enzyme inducing agents is essential in order to obtain bacterium cells having a high nitrile hydratase activity in a high yield as will be apparent from the experimental examples set forth hereinlater. Ordinarily, the concentration of the enzyme inducing agent in the culture medium is adjusted preferably to lower than 15 g/l (in total when two or more compounds are used as such), and more preferably to 10 g/l or lower although this may vary depending on the cultivation time, temperature and other conditions. If the concentration becomes 15 g/l or higher, the nitrile hydratase activity of the bacteria will be lowered. The pH of the culture medium is of the order of 6 to 9, preferably of the order of 7 to 8, while the cultivation temperature is of the order of 20° to 37° C., preferably of the order of 25° to 30° C., and the cultivation time is about 1 to 3 days.

After the cultivation has been completed, the cells or nitrile hydratase can be collected or utilized in accordance with a procedure which will be described hereinlater in the experimental examples.

In the disclosure, the letter "l" indicates "liter".

Experimental Examples

In the following experimental examples, 1 ml of a culture fluid was added to 9 ml of a phosphate buffer solution (pH 7.5) containing 2.8% by weight of acrylonitrile, and the resulting solution was caused to react at 10° C. for 10 to 60 minutes. The quantity of acrylamide obtained was measured by means of gas chromatography, and the hydratase activity of the bacteria exhibited in the hydration of acrylonitrile was determined on the basis of the data thus obtained, the capability of producing 1 μmole of acrylamide per ml of a culture fluid per minute being designated as 1 unit.

EXAMPLE 1

100 ml of a precultivation culture medium (pH 7.2) comprising 10 g/l of glucose, 5 g/l of peptone, 3 g/l of yeast extract, and 3 g/l of malt extract was sterilized in a 500-ml Erlenmeyer flask. *Pseudomonas chlororaphis*, strain B 23 (FERM BP-187), was inoculated into the sterilized culture medium, and subjected to shaking cultivation at 25° C. for 24 hours.

Separately, 100 ml of a culture medium (pH 7.2) comprising 10 g/l of sucrose, 0.5 g/l of $KH_2PO_4$, 0.5 g/l of $K_2HPO_4$, 0.5 g/l of $MgSO_4.7H_2O$, and 10 mg/l of $FeSO_4.7H_2O$ was sterilized in a 500-ml Erlenmeyer flask.

Into this culture medium was inoculated 1 ml of the seed culture fluid obtained by the precultivation, and shaking cultivation was carried out aerobically at 25° C. with sequential addition of isobutyronitrile and isobutyramide as an enzyme inducing agent respectively in two instances.

For comparison purposes, cultivation was carried out similarly with the addition of the enzyme inducing agent at one time in a single batch.

The culture fluids obtained by the foregoing cultivation procedures carried out for specific time periods were sampled respectively, and the nitrile hydratase activity of each of the culture fluid samples exhibited in the hydration of acrylonitrile was measured.

The relationship between the conditions under which the enzyme inducing agents were added and the nitrile hydratase activities of the culture fluids is shown in Table 1.

TABLE 1

| Species | Enzyme Inducing Agent | | | Nitrile Hydratase Activity (unit) Time Period After the Initiation of Cultivation (hr) | | |
|---------|----------------------|----------------------|----------|------|------|------|
| | Way of Addition | Time of Addition [Time period after the initiation of cultivation (hr)] | Quantity (g/100 ml) | 12 | 24 | 40 |
| | | 0 | 0.24 | | | |
| | Sequential | 7 | 0.24 | | | |
| | addition | 15 | 0.24 | 6.2 | 20.5 | 43.5 |
| | | 30 hr | 0.24 | | | |
| | | 0 | 0.24 | | | |
| Isobutyro- | Sequential | 7 | 0.24 | | | |
| nitrile | addition | 15 | 0.24 | 6.9 | 22.1 | 9.2 |
| | | 30 | 1.6 | | | |
| | One-Step | 0 | 0.4 | 6.1 | 15.1 | 22.3 |
| | Addition | 0 | 0.8 | 5.2 | 17.6 | 24.5 |
| | (Com. Ex.) | 0 | 1.6 | ≦0.1 | ≦0.1 | 0.4 |
| | | 0 | 0.25 | | | |
| | Sequential | 7 | 0.25 | | | |
| | addition | 15 | 0.25 | 5.8 | 18.3 | 39.7 |
| | | 30 | 0.25 | | | |
| | | 0 | 0.25 | | | |
| Isobutyr- | Sequential | 7 | 0.25 | | | |
| amide | addition | 15 | 0.25 | 5.1 | 19.4 | 13.2 |
| | | 30 | 1.5 | | | |
| | One-Step | 0 | 0.5 | 5.6 | 11.3 | 21.8 |
| | Addition | 0 | 1.0 | 6.2 | 13.4 | 23.9 |
| | (Com. Ex.) | 0 | 2.0 | ≦0.1 | 0.6 | 5.5 |

As is apparent from Table 1, the enzymatic activity of the culture fluid obtained when isobutyronitrile or isobutyramide was added sequentially increased to a value nearly twice that obtained when substantially the same quantity of the enzyme inducing agent was added at one time. In the case where the concentration of the enzyme inducing agent exceeds 15 g/l during cultivation (30 hours after the initiation of cultivation), however, the enzymatic activity decreased afterward even when the enzyme inducing agent was added sequentially.

When the enzyme inducing agent was added at one time at the initiation of the cultivation at a concentration of 15 g/l or higher, almost no enzymatic activity was exhibited.

EXAMPLE 2

100 ml of a precultivation culture medium (pH 7.2) comprising 10 g/l of glucose, 5 g/l of peptone, 3 g/l of yeast extract, and 3 g/l of malt extract was sterilized in a 500-ml Erlenmeyer flask. Pseudomonas sp., strain PS-1 (FERM BP-188), was inoculated into the sterilized culture medium, and subjected to shaking cultivation at 25° C. for 24 hours.

Separately, 100 ml of a culture medium (pH 7.2) comprising 10 g/l of glycerol, 0.5 g/l of $KH_2PO_4$, 0.5 g/l of $K_2HPO_4$, 0.5 g/l of $MgSO_4 \cdot 7H_2O$, and 10 mg/l of $FeSO_4 \cdot 7H_2O$ was sterilized in a 500-ml Erlenmeyer flask.

This culture medium was inoculated with 1 ml of the seed culture fluid obtained by the precultivation, and shaking cultivation was carried out aerobically at 25° C. with sequential addition of propionitrile and propionamide as an enzyme inducing agent respectively in two instances.

For comparison purposes, cultivation was carried out similarly with addition of the enzyme inducing agent at one time in a single batch.

The nitrile hydratase activity of each of the culture fluids after the elapse of specific time periods exhibited in the hydration of acrylonitrile was measured.

The relationship between the conditions under which the enzyme inducing agents were added and the nitrile hydratase activities of the culture fluids is summarized in Table 2.

TABLE 2

| Species | Enzyme Inducing Agent | | | Nitrile Hydratase Activity (unit) Time Period After the Initiation of Cultivation (hr) | | |
|---------|----------------------|----------------------|----------|------|------|------|
| | Way of Addition | Time of Addition [Time period after the initiation of cultivation (hr)] | Quantity (g/100 ml) | 12 | 24 | 40 |
| | | 0 | 0.24 | | | |
| | Sequential | 7 | 0.24 | | | |
| | addition | 15 | 0.24 | 4.6 | 19.6 | 34.8 |
| Propio- | | 30 | 0.24 | | | |
| nitrile | | | | | | |
| | One-step | 0 | 0.8 | 3.2 | 7.8 | 16.9 |
| | addition | | | | | |
| | (Com. Ex.) | 0 | 1.6 | ≦0.1 | ≦0.1 | 0.2 |
| | | 0 | 0.25 | | | |
| | | 7 | 0.25 | | | |
| | Sequential | | | | | |
| Propion- | addition | 15 | 0.25 | 4.1 | 17.8 | 30.9 |
| amide | | 30 | 0.25 | | | |

TABLE 2-continued

| Species | Enzyme Inducing Agent | | | Nitrile Hydratase Activity (unit) Time Period After the Initiation of Cultivation (hr) | | |
|---|---|---|---|---|---|---|
| | Way of Addition | Time of Addition [Time period after the initiation of cultivation (hr)] | Quantity (g/100 ml) | 12 | 24 | 40 |
| | One-step addition (Com. Ex.) | 0 | 0.5 | 2.7 | 6.1 | 15.2 |
| | | 0 | 1.0 | 3.0 | 7.5 | 16.0 |

As is apparent from Table 2, the enzymatic activity of the culture fluid obtained when propionitrile or propionamide was added sequentially increased to a value nearly twice that obtained when substantially the same quantity of the enzyme inducing agent was added at one time.

EXAMPLE 3

1.3 l of a culture medium (pH 7.2) comprising 20 g/l of sucrose, 1 g/l of KH$_2$PO$_4$, 1 g/l of K$_2$HPO$_4$, 1 g/l of MgSO$_4$.7H$_2$O, and 20 mg/l of FeSO$_4$.7H$_2$O dissolved in tap water was sterilized in a small-sized 2-l jar fermenter.

This culture medium was inoculated with 50 ml of a seed culture fluid obtained similarly as in Example 1 by the precultivation of *Pseudomonas chlororaphis*, strain B 23 (FERM BP-187), and cultivation was carried out at 25° C. for 45 hours at an aeration rate of 2 l/min. and an agitation speed of 500 rpm. Isobutyronitrile was added intermittently in a quantity amounting to a total of 20.8 g/1.3 l by the completion of the cultivation while the concentration thereof in the culture fluid was controlled so as not to exceed 10 g/l. The pH of the culture fluid was adjusted to 7 to 8 with an aqueous solution of sulfuric acid or caustic soda.

For comparison purposes, cultivation was carried out similarly except that 5.2 g/1.3 l of isobutyronitrile was added at one time at the initiation of the cultivation.

In the case where isobutyronitrile was added sequentially, the nitrile hydratase activity reached 166 units (the cell concentration being 7.8 g/l) after 45 hours' cultivation while, in the case where this enzyme inducing agent was at one time, the nitrile hydratase activity reached the maximum (14 units) 12 hours after the initiation of the cultivation and then started to decrease to 12 units (the cell concentration being 4.2 g/l) as measured after 45 hours' cultivation.

EXAMPLE 4

The procedure of Example 2 was followed except that a total of 24.7 g/1.3 l of isobutyronitrile was added through a pump continuously over a period of 40 hours while the concentration thereof in the culture fluid was controlled so as not to exceed 10 g/l.

As a result, 171 units (the cell concentration being 7.4 g/l) of nitrile hydratase activity was obtained after 44 hours' cultivation.

EXAMPLE 5

1.3 l of a culture medium (pH 7.2) comprising 25 g/l of glucose, 2 g/l of ammonium sulfate, 1 g/l of KH$_2$PO$_4$, 1 g/l of K$_2$HPO$_4$, 1 g/l of MgSO$_4$.7H$_2$O, and 20 mg/l of FeSO$_4$.7H$_2$O dissolved in tap water was sterilized in a small-sized 2-l jar fermenter.

This culture medium was inoculated with 50 ml of a seed culture fluid obtained similarly as in Example 1 by the precultivation of *Pseudomonas chlororaphis*, strain B 23 (FERM BP-187), and cultivation was carried out at 25° C. for 42 hours at an aeration rate of 2 l/min. and an agitation speed of 500 rpm. The pH of the culture fluid was adjusted to 7 to 8 with an aqueous solution of sulfuric acid or caustic soda. A total of 20.8 g/1.3 l of isobutyronitrile was added intermittently from 8 hours after the initiation of the cultivation until the completion thereof, while the concentration of the isobutyronitrile in the culture fluid was controlled so as not to exceed 10 g/l.

For comparison purposes, cultivation was conducted similarly except that 10.4 g/1.3 l of isobutyronitrile was added at one time 8 hours after the initiation of the cultivation.

In the case where isobutyronitrile was added sequentially, 170 units (the cell concentration being 9.0 g/l) of nitrile hydratase activity was obtained after 42 hours' cultivation, while, in the case where this enzyme inducing agent was added at one time, the nitrile hydratase activity reached 42 units 27 hours after the initiation of the cultivation and then started to decrease to 30 units (the cell concentration being 6.7 g/l) as measured after 42 hours' cultivation.

We claim:

1. In a method of cultivating Pseudomonas bacteria having nitrile hydratase activity by reproducing and proliferating said bacteria in a culture medium and then using said nitrile hydratase to hydrate a nitrile to an amide, the improvement wherein at least one compound selected from the group consisting of propionitrile, isobutyronitrile, propionamide and isobutyramide is added continuously or incrementally, but not in one batch at one time, to the culture medium during the reproduction and proliferation of cells of the Pseudomonas bacteria in an amount effective to increase the nitrile hydratase activity per unit of culture fluid of the culture medium.

2. The method of claim 1, wherein the total concentration of the added compound selected from at least one member of the group consisting of propionitrile, isobutyronitrile, propionamide and isobutyramide in the culture medium throughout the reproduction and proliferation of cells of bacteria having nitrile hydratase activity is lower than 15 g./l.

3. The method as claimed in claim 1, wherein the Pseudomonas bacterium having nitrile hydratase activity is *Pseudomonas chlororaphis*, strain B 23 (FERM BP-187), or Pseudomonas sp., strain PS 1 (FERM BP-188).

4. The method as claimed in claim 1 wherein the compound selected from at least one member of the group consisting of propionitrile, isobutyronitrile, propionamide and isobutyramide is added continuously to the culture medium.

5. The method as claimed in claim 1 wherein the compound selected from at least one member of the group consisting of propionitrile, isobutyronitrile, propionamide and isobutyramide is added incrementally in a plurality of portions to the culture medium.

6. The method as claimed in claim 1 in which at least one compound selected from the group consisting of propionitrile, isobutyronitrile, propionamide and isobutyramide is added incrementally in a plurality of portions or continuously to the culture medium in an amount effective to increase the nitrile hydratase activity per unit of culture fluid of the culture medium, and wherein the total concentration of said compound in the culture medium is lower than 15 g/l throughout the cultivation.

7. The method as claimed in claim 1, wherein the total concentration of the added compound selected from at least one member of the group consisting of propionitrile, isobutyronitrile, propionamide, and isobutyramide in the culture medium throughout the cultivation is lower than 10 g/l.

8. The method as claimed in claim 1, wherein propionitrile is added continuously or incrementally to the culture medium during the reproduction proliferation of cells of bacteria having nitrile hydratase activity.

9. The method as claimed in claim 1, wherein isobutyronitrile is added continuously or incrementally to the culture medium during the reproduction and proliferation of cells of bacteria having nitrile hydratase activity.

10. The method as claimed in claim 1, wherein propionamide is added continuously or incrementally to the culture medium during the reproduction and proliferation of cells of bacteria having nitrile hydratase activity.

11. The method as claimed in claim 1, wherein isobutyramide is added continuously or incrementally to the culture medium during the reproduction and proliferation of cells of bacteria having nitrile hydratase activity.

* * * * *